(12) United States Patent
Burke et al.

(10) Patent No.: US 7,670,997 B2
(45) Date of Patent: Mar. 2, 2010

(54) OPHTHALMIC COMPOSITIONS COMPRISING A BRANCHED, GLYCEROL MONOALKYL COMPOUND AND A FATTY ACID MONOESTER

(75) Inventors: Susan E. Burke, Batavia, NY (US); Eric Phillips, Ontario, NY (US); Fang Zhao, Rochester, NY (US); Vicki Barniak, Fairport, NY (US); Joseph C. Salamone, Boca Raton, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 145 days.

(21) Appl. No.: 11/691,125

(22) Filed: Mar. 26, 2007

(65) Prior Publication Data

US 2007/0286767 A1    Dec. 13, 2007

Related U.S. Application Data

(60) Provisional application No. 60/811,828, filed on Jun. 8, 2006.

(51) Int. Cl.
 C11D 3/48    (2006.01)
 C11D 3/44    (2006.01)

(52) U.S. Cl. ............... 510/112; 510/131; 510/382; 510/384; 510/437; 134/901

(58) Field of Classification Search ............ 510/112, 510/382, 384, 131, 437; 134/901
 See application file for complete search history.

(56) References Cited

U.S. PATENT DOCUMENTS

| | | | |
|---|---|---|---|
| 4,002,775 A | 1/1977 | Kabara et al. | |
| 4,997,851 A | 3/1991 | Isaacs et al. | |
| 5,516,510 A | 5/1996 | Beilfuss et al. | |
| 5,624,958 A | 4/1997 | Isaacs et al. | |
| 5,885,562 A | 3/1999 | Lowry et al. | |
| 5,906,831 A | 5/1999 | Larsson et al. | |
| 6,040,347 A | 3/2000 | Cupferman et al. | |
| 6,468,551 B1 * | 10/2002 | Diec et al. | 424/401 |
| 2002/0141899 A1 | 10/2002 | Tsao | |
| 2002/0146375 A1 * | 10/2002 | Schreiber et al. | 424/59 |
| 2004/0059006 A1 * | 3/2004 | Beilfuss et al. | 514/718 |
| 2004/0167218 A1 | 8/2004 | Sly | |
| 2004/0208908 A1 | 10/2004 | Modak et al. | |
| 2004/0247685 A1 * | 12/2004 | Modak et al. | 424/488 |
| 2005/0084471 A1 * | 4/2005 | Andrews et al. | 424/70.31 |
| 2005/0095281 A1 * | 5/2005 | Hofland et al. | 424/450 |
| 2005/0154067 A1 * | 7/2005 | Beilfuss et al. | 514/715 |
| 2005/0159331 A1 * | 7/2005 | Tamura et al. | 510/512 |
| 2005/0222276 A1 * | 10/2005 | Schmaus et al. | 514/738 |
| 2006/0257342 A1 * | 11/2006 | Mu et al. | 424/63 |
| 2007/0020342 A1 * | 1/2007 | Modak et al. | 424/642 |
| 2007/0054967 A1 * | 3/2007 | Schmaus et al. | 514/717 |
| 2007/0287752 A1 * | 12/2007 | Burke et al. | 514/625 |
| 2008/0033021 A1 * | 2/2008 | Burke | 514/358 |

FOREIGN PATENT DOCUMENTS

WO    99/11237 A    3/1999

OTHER PUBLICATIONS

Bergsson et al., *In Vitro Killing of Candida albicans by Fatty Acids and Monoglycerides*, Antimicrobial Agents and Chemotherapy, pp. 3209-3212 (Nov. 2001).
Thormar et al., *Hydrogels Containing Monocaprin Have Potent Microbicidal Activities Against Sexually Transmitted Viruses and Bacteria In Vitro*, Sex Transm Inf, 75, pp. 181-185 (1999).
Thorgeirsdottir et al., *Antimicrobial Activity of Monocaprin: A Monoglyceride with Potential Use As a Denture Disinfectant*, Acta Odontologica, vol. 64, No. 1, pp. 21-26 (Feb. 2006).
International Search Report (PCTISA/210) and Written Opinion (PCT/ISA/237) mailed on May 26, 2008.

* cited by examiner

Primary Examiner—Charles I Boyer

(57) ABSTRACT

An aqueous ophthalmic composition comprising a branched, glycerol monoalkyl compound and a fatty acid monoester. The fatty acid monoester comprises an aliphatic fatty acid portion having six to fourteen carbon atoms and an aliphatic hydroxyl portion. The composition will also have an osmolality in a range from 200 mOsmol/kg to 400 mOsmol/kg. The invention is also directed to a method of inhibiting the formation of foam in an aqueous ophthalmic composition that includes a surfactant as well as to a method of enhancing the biocidal efficacy of an aqueous ophthalmic composition containing a fatty acid monoester.

17 Claims, No Drawings

OPHTHALMIC COMPOSITIONS COMPRISING A BRANCHED, GLYCEROL MONOALKYL COMPOUND AND A FATTY ACID MONOESTER

This application claims priority to U.S. provisional application Ser. No. 60/811,828 filed Jun. 8, 2006, the entire disclosure of which is incorporated herein by reference.

The invention relates to aqueous ophthalmic compositions comprising a branched, glycerol monoalkyl compound and a fatty acid monoester. The invention is also directed to adjusting the surface tension properties, or enhancing the biocidal efficacy, of ophthalmic compositions.

BACKGROUND OF THE INVENTION

Aqueous ophthalmic solutions are typically applied to eyes in the form of drops, or used to treat contact lenses that are then subsequently placed in the eye. The primary functions of these solutions are to provide a moisturizing effect for eyes, or to clean, disinfect or wet contact lenses. Given these primary functions, ophthalmic solutions will include one or more surfactants that function as cleaning agents. The surfactants, however, also affect the surface tension properties of aqueous solutions, and in general, will increase the tendency of the solutions to foam. As used herein, a foam is a dispersion of a gas bubbles that form or are present in an aqueous ophthalmic solution. The gas bubbles are separated from the liquid by thin liquid films called lamellae. Ordinarily, the bubbles will burst at a thickness of approximately 10 nm, and this phenomenon is referred to as drainage. Drainage occurs almost instantaneously in pure water. On the other hand, surfactants tend to stabilize the lamellae against rupture, thereby facilitating foam formation and increasing foam stability in aqueous solutions.

The foam-forming tendency and foam properties are dependent on the type and concentration of surfactant in the solution. For example, surfactants that enhance foam formation include several members from the family of polyethers known as Pluronic® and Tetronic® surfactants. In particular, Pluronic® F-127 and Tetronic® 1107 are conventionally used as cleaning agents in ophthalmic solutions. Even at relatively low concentrations, e.g., less than 1% by weight, Pluronic® F-127 and Tetronic® 1107 surfactants can cause ophthalmic compositions to foam. U.S. Pat. No. 6,790,816 indicates that undesirable amounts of foaming can be avoided in compositions containing Tetronic® 1107 by simply reducing the amount of agitation of such products. See, also U.S. Patent Publication No. 2002/0141899.

Formulating aqueous ophthalmic solutions to minimize foaming can present a challenge from the perspective of both manufacturing and consumer satisfaction. For example, solution foaming increases production costs by reducing manufacturing process throughput and material handling speeds. Ophthalmic solutions that foam can also cause product handling to be more difficult for the consumer.

Octoxyglycerin (3-[(2-ethylhexyl)oxy]-1,2-propanediol), sold under the trade name Sensiva® SC50 (Schulke & Mayr), is a glycerol alkyl monoether known to be gentle to the skin. Octoxyglycerine is said to exhibit antimicrobial activity against a variety of Gram-positive bacteria associated with perspiration odor, such as *Micrococcus luteus, Corynebacterium aquaticum, Corynebacterium flavescens, Corynebacterium callunae*, and *Corynebacterium nephredi*, and is used in various skin deodorant preparations at concentrations between about 0.2 and 3% by weight (Sensiva® product literature, Schulke & Mayr).

U.S. Pat. No. 5,885,562 to Lowry et al., describes deodorant compositions comprising an antimicrobial agent, namely polyhexamethylene biguanide at a concentration of between 0.01% and 0.5% by weight, together with a polarity modifier such as Sensiva® SC50 at concentrations of 1% to 15% by weight. The compositions can also comprise a short chain monohydric alcohol such as ethanol from 20% to 80% by weight. U.S. Pat. No. 5,516,510 by Beilfuss et al. also describes deodorant compositions that comprise glycerin monoalkyl ethers, and in particular, octoxyglycerin. The deodorant compositions are said to be formulated in aqueous or alcoholic solutions and can include additional antimicrobial compounds, including triclosan, chlorhexidine salts, alexidine salts, biguanides and phenoxyethanol.

SUMMARY OF THE INVENTION

The invention is directed to an aqueous ophthalmic composition comprising a branched, glycerol monoalkyl compound and a fatty acid monoester. The fatty acid monoester comprises an aliphatic fatty acid portion having six to fourteen carbon atoms and an aliphatic hydroxyl portion. The composition will also have an osmolality in a range from 200 mOsmol/kg to 400 mOsmol/kg.

The invention is also directed to a method of inhibiting the formation of foam in an aqueous ophthalmic composition that includes a surfactant. The method comprises adding a branched, glycerol monoalkyl compound to the composition in an amount from 0.05 ppm to 30.0 ppm to inhibit the formation of foam or to destabilize foam in the composition. Again, the composition will have an osmolality in a range from 200 mOsmol/kg to 400 mOsmol/kg.

The invention is also directed to a method of enhancing the biocidal efficacy of an aqueous ophthalmic composition containing a fatty acid monoester. The method comprises adding a branched, glycerol monoalkyl compound to the composition. The fatty acid monoester comprises an aliphatic fatty acid portion having six to fourteen carbon atoms and an aliphatic hydroxyl portion. Again, the composition will have an osmolality in a range from 200 mOsmol/kg to 400 mOsmol/kg.

DETAILED DESCRIPTION OF THE INVENTION

The invention is directed to an aqueous ophthalmic composition comprising a branched, glycerol monoalkyl compound and a fatty acid monoester. The fatty acid monoester comprises an aliphatic fatty acid portion having six to fourteen carbon atoms and an aliphatic hydroxyl portion. The composition will also have an osmolality in a range from 200 mOsmol/kg to 400 mOsmol/kg. As used herein, the term "ophthalmic composition" denotes a composition intended for application in the eye or intended for treating a device to be placed in contact with the eye such as a contact lens.

In many embodiments of the invention, the branched, glycerol monoalkyl compound is selected from a branched, glycerol monoalkyl ether, a branched, glycerol monoalkyl amine or a branched, glycerol monoalkyl sulfide, or any mixture thereof. For example, each of the respective monoalkyl ether, monoalkyl amine and monoalkyl sulfide can be 3-[(2-ethylhexyl)oxy]-1,2-propanediol (EHOPD), 3-[(2-ethylhexyl)amino]-1,2-propanediol (EHAPD), 3-[(2-ethylhexyl)thiol]-1,2-propanediol (EHSPD) or any mixture thereof. The chemical structures of EHOPD, EHAPD and EHSPD are provided below.

EHOPD is also referred to as octoxyglycerin as is sold under the tradename Sensiva® SC50 (Schulke & Mayr).

EHOPD is a glycerol alkyl ether known to be gentle to the skin, and to exhibit antimicrobial activity against a variety of Gram-positive bacteria such as *Micrococcus luteus, Corynebacterium aquaticum, Corynebacterium flavescens, Corynebacterium callunae*, and *Corynebacterium nephredi*. Accordingly, EHOPD is used in various skin deodorant preparations at concentrations between about 0.2 and 3 percent by weight. EHAPD can be prepared from ethylhexylamine and 2,3-epoxy-1-propanediol using chemistry well known to those of ordinary skill in the art. EHSPD can be prepared from 2-ethylhexylthiol and 2,3-epoxy-1-propanediol using chemistry well known to those of ordinary skill in the art.

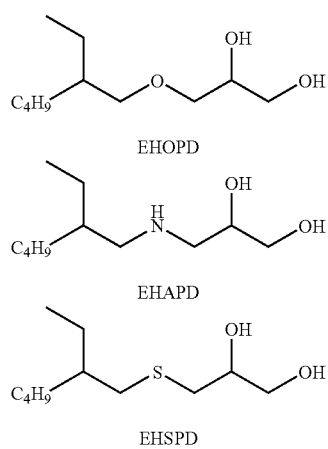

The lens care compositions also comprise a fatty acid monoester, in which the fatty acid monoester comprises an aliphatic fatty acid portion having six to fourteen carbon atoms, and an aliphatic hydroxyl portion. The term "aliphatic" refers to a straight or branched, saturated or unsaturated hydrocarbon.

In one embodiment, the aliphatic fatty acid portion is a straight chain, saturated or unsaturated hydrocarbon with eight to ten carbons. In another embodiment, the aliphatic fatty acid portion is a branched chain, saturated or unsaturated hydrocarbon with eight to ten carbons. For example, a 5-ethyl substituted derivative of decanoylglycerol can be used.

Furthermore, if the fatty acid portion is unsaturated, it is preferred that the fatty acid is monounsaturated, with the cis-form being preferred over the trans-form.

The aliphatic hydroxyl portion of the fatty acid monoester can be any aliphatic compound with at least one hydroxyl group, preferably at least two hydroxyl groups. In many of the embodiments, the aliphatic hydroxyl portion will have from three to nine carbons.

The aliphatic hydroxyl portion includes, but is not limited to, propylene glycol, glycerol, a polyalkylene glycol, e.g., polyethylene glycol or polypropylene glycol, a cyclic polyol, e.g., sorbitan, glucose, mannose, sucrose, fructose, fucose and inisitol and derivatives thereof, and a linear polyol, e.g., mannitol and sorbitol and derivatives thereof. In a preferred embodiment the aliphatic hydroxyl portion is glycerol.

The invention is also directed to adjusting the surface tension properties of the ophthalmic composition by the presence of a branched glycerol monoalkyl compound. In addition to its stated effect on the antimicrobial efficacy of ophthalmic compositions, applicants have discovered that by adding small amounts of a glycerol monoalkyl compound to ophthalmic compositions the amount of foam produced during manufacturing, or the amount of foaming observed by the consumer during handling, is significantly reduced. Also, the glycerol monoalkyl compound tends to reduce the tenacity of the foam that does develop, meaning that the foam is more easily disrupted. For example, applicants have observed that the glycerol monoalkyl compound can hasten the drainage of what small amount of foam does form upon agitation of an ophthalmic composition. Without being bound by theory, it is believed that the lamellae walls of the bubbles within the foam are destabilized by the amphiphilic nature of the glycerol monoalkyl compound. The glycerol monoalkyl compound either spreads over the lamellae film causing an increase in surface tension, or the individual molecules penetrate the lamellae leading to a decrease in cohesion in the film. Both mechanisms can lead to destabilization and eventual rupture of the lamellae, thereby disrupting foam formation and promoting foam drainage.

If used primarily as an anti-foaming agent, the total amount of glycerol monoalkyl compound in an ophthalmic composition will range from 0.05 ppm to 30.0 ppm. If the glycerol monoalkyl compound is to be used as an antimicrobial agent or to enhance the antimicrobial efficacy of an antimicrobial component, than higher concentrations of the glycerol monoalkyl compound can be used. Accordingly, ophthalmic compositions can comprise a total of from 0.05 ppm to 1,000 ppm or from 1 ppm to 500 ppm, of glycerol monoalkyl compound.

The ophthalmic compositions can also include an antimicrobial component. Most of the preferred compositions will include a cationic antimicrobial component. The cationic antimicrobial components include chemicals which derive their antimicrobial activity through a chemical or physiochemical interaction with microbes or microorganisms such as those contaminating a contact lens. Suitable cationic antimicrobial components are those generally employed in ophthalmic applications and include, but are not limited to, quaternary ammonium salts used in ophthalmic applications such as poly[dimethylimino-2-butene-1,4-diyl]chloride, α-[4-tris(2-hydroxyethyl)ammonium chloride-2-butenyl]poly[1-dimethylammonium chloride-2-butenyl]-ω-tris(2-hydroxyethyl)ammonium chloride (CAS# 68518-54-7, available as Polyquatemium-1® from Onyx Corporation), myristamidopropyl dimethylamine (Aldox®), benzalkonium halides, and biguanides such as salts of alexidine, alexidine-free base, salts of chlorhexidine, hexamethylene biguanides and salts thereof and their polymers such as poly(hexamethylene biguanide) (PHMB) or PHMB-CG*, antimicrobial polypeptides and mixtures thereof. An exemplary list of cationic disinfecting antimicrobial components include myristamidopropyl dimethylamine, α-[4-tris(2-hydroxyethyl)ammonium chloride-2-butenyl]poly[1-dimethylammonium chloride-2-butenyl]-ω-tris(2-hydroxyethyl)ammonium chloride, poly(hexamethylene biguanide) (PHMB), PHMB-CG*, and any mixture thereof.

The term "cationic" when referring to an antimicrobial component refers to the predominant form of the antimicrobial component at neutral pH having a positive charge and a counteranion.

The antimicrobial component can be any ophthalmically acceptable, compound that is effective to disinfect a contact lens contacted with the lens care compositions. The term "ophthalmically acceptable" means that the component is compatible with ocular tissue, that is, it does not cause significant or undue detrimental effects when brought into contact with ocular tissue.

PHMB is best described as a polymeric biguanide composition comprising at least six biguanide polymers each with a different combination of terminal guanidine, cyanoguanidino or amine terminal groups. Accordingly, a commercial sample of PHMB will likely comprise a mixture of various polymeric biguanides with the three mentioned terminal groups. The biguanaides differ with respect to which terminal groups are arranged on the polymer and what are the molar concentrations of each terminal group in the mixture. PHMB (Cosmocil® type PHMB) can contain from 20 mol % to 30 mol % terminal amine groups. The molar concentration of terminal guanidine groups and terminal cyanoguanidino groups range from 38 mol % to 49 mol % and 30 mol % to 32 mol %, respectively A new synthetic route to polymeric biguanide compositions is described in copending U.S. provisional application Ser. Nos. 60/853,579 filed Oct. 23, 2006, and 60/895,770 filed Mar. 20, 2007. The new synthetic route provides a polymeric biguanide composition comprising less than 18 mol % of terminal amine groups as measured by $^{13}C$ NMR. The polymeric biguanide composition also is characterized by a relative increase in the molar concentration of terminal guanidine groups or terminal cyanoguanidino groups. For example, in one embodiment, the biguanide composition comprises less than 18 mol % of terminal amine groups, and 55 mol % or greater of terminal guanidine groups. In another embodiment, the biguanide composition comprises less than 18 mol % of terminal amine groups, and 40 mol % or greater of terminal cyanoguanidino groups.

In this application we refer to this novel polymeric biguanide composition as PHMB-CG*. We also refer to polymeric biguanide compositions in the generic sense as "hexamethylene biguanides", which one of ordinary skill in the art would recognize to include both PHMB as well as PHMB-CG*.

The amount of antimicrobial component present in the compositions will depend upon the type of antimicrobial component as well as the ophthalmic application for the solution. If the composition is to be used to treat contact lenses, then the amount used is effective in disinfecting the contact lenses, while at the same time promote lens patient comfort and acceptability. Typically, an amount of antimicrobial component is used to reduce the microbial burden or load on the contact lens by one log order in four hours. More preferably, an effective amount of antimicrobial component reduces the microbial load by one log order in one hour. The reductions are based upon similarly prepared lens solutions absent the cationic antimicrobial component.

In one embodiment, the primary antimicrobial component present in the lens care compositions is poly(hexamethylene biguanide) or PHMB-CG*, which is present from 0.01 ppm to 3 ppm. In another embodiment, the primary antimicrobial component present in the lens care compositions is α-[4-tris (2-hydroxyethyl)ammonium chloride-2-butenyl]poly[1-dimethylammonium chloride-2-butenyl]-ω-tris(2-hydroxyethyl)ammonium chloride, which is present from 1 ppm to 100 ppm. Any one mixture of the two cationic antimicrobial components can also be present in the lens care compositions.

The lens care compositions can also include dexpanthenol, which is an alcohol of pantothenic acid, also called Provitamin B5, D-pantothenyl alcohol or D-panthenol. In some formulations of the lens care compositions, dexpanthenol can exhibit good cleansing action and can stabilize the lachrymal film at the eye surface when placing the contact lenses on the eye. Dexpanthenol is preferably present in the contact lens care compositions in an amount from 0.2% to 10% (w/v), from 0.5% to 5% (w/v), or from 1% to 3% (w/v).

The lens care compositions can also include sorbitol, which is a hexavalent sugar alcohol. Typically, dexpanthenol is used in combination with sorbitol. In specific formulations the combination dexpanthenol and sorbitol can provide enhanced cleansing action and can also stabilize the lachrymal film following placement of the contact lens on the eye. These formulations help guard against the appearance of dryness, and can substantially improve patient comfort when wearing contact lenses. Negative effects caused by surface-active substances and preservatives are reduced, and the drying out of the lenses can be minimized. Sorbitol is present in the lens care compositions in an amount from 0.4% to 10% (w/v), from 0.8% to 6% (w/v), or from 1% to 3% (w/v).

The contact lens care compositions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v), or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4. The buffer system in the composition is used to maintain the pH of the composition in the range from 6.5 to 8.0.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing a polyaminopropyl biguanide (PAPB), also known as polyhexamethylene biguanide (PHMB), has enhanced efficacy when combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Additional buffer substance may optionally be added to the composition. For example, traditionally known buffers include, for example, citrates, citric acid, sodium bicarbonate, TRIS, and the like. Other ingredients in the solution, while having other functions, may also affect the buffer capacity. For example, EDTA, often used as a complexing agent, can have a noticeable effect on the buffer capacity of a composition.

A preferred buffer system is based upon boric acid/borate, a mono and/or dibasic phosphate salt/phosphoric acid or a combined boric/phosphate buffer system. For example a combined boric/phosphate buffer system can be formulated from a mixture of sodium borate and phosphoric acid or the combination of sodium borate and the monobasic phosphate.

In a combined boric/phosphate buffer system, the solution comprises about 0.05 to 2.5% (w/v) of a phosphoric acid or its salt and 0.1 to 5.0% (w/v) of boric acid or its salt. The phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care compositions can also include a water-soluble borate-polyol complex which can be formed by mixing a source of borate with a polyol of choice in an aqueous solution. These complexes can be used in conjunction with the cationic antimicrobial component above, and can help to meet preservative efficacy and disinfection standards. In such compositions, the molar ratio of borate to polyol is generally from 1:0.1 to 1:10, or from 1:0.25 to 1:2.5. If present in the lens care compositions, the borate-polyol complex is usually present from 0.5% to 5% (w/v), from 1.0% to 2.5% (w/v). The borate-polyol complexes are described in greater detail in U.S. Pat. No. 6,143,799.

The present compositions preferably further comprise effective amounts of one or more additional components, such as a detergent or surfactant component; a viscosity inducing or thickening component; a chelating or sequestering component; a tonicity component and mixtures thereof. The additional component or components can be selected from materials which are known to be useful in contact lens care compositions and are included in amounts effective to provide the desired effect or benefit. When an additional component is included, it is preferably compatible under typical use and storage conditions with the other components of the composition.

Suitable surfactants can be either amphoteric, cationic, anionic, or nonionic, and are typically present (individually or in combination) in amounts up to 15%, or up to 5% (w/v). One preferred surfactant class are the amphoteric or nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of the class include polysorbate 20 (available under the trademark Tween® 20), polyoxyethylene (23) lauryl ether (Brij® 35) and polyoxyethylene glycol stearates such as polyoxyethyene (40) stearate (Myrj®52), polyoxyethylene (25) propylene glycol stearate (Atlas® G 2612). Still other preferred surfactants include tyloxapol, betaine-type surfactants, polysulfates, polyethylene glycol, alkyl esters and any mixture thereof.

A particular non-ionic surfactant consisting of a poly(oxypropylene)-poly(oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under Tetronic®.

An analogous of series of surfactants, for use in the lens care compositions, is the poloxamer series which is a poly(oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237.

Suitable normally high-foaming surfactants include, for example, but are not limited to polyethers based upon poly(ethylene oxide) and/or poly(propylene oxide) often referred to the polaxomer or polaxamine class of surfactants. One such type of surfactant comprises poly(ethylene oxide)-poly(propylene oxide)-poly(ethylene oxide) (PEO-PPO-PEO), or poly(propylene oxide)-poly(ethylene oxide)-poly(propylene oxide), i.e., (PPO-PEO-PPO), polyethers. Another such type of surfactant comprises poly(ethylene oxide) and/or poly(propylene oxide) adducts of ethylene diamine. Surfactant materials of the foregoing types are commercially available under the trade names Pluronics™, R-Pluronics™, Tetronics™ and R-Tetronics™ (BASE Wyandotte Corp., Wyandotte, Mich.) and are further described in U.S. Pat. No. 4,820,352.

The Pluronic® F-127 and Tetronic® 1107. Pluronic® F-127 has the general structure $(EO)_{97}(PO)_{69}(EO)_{97}$ and a molecular weight of about 12,600. Tetronic® 1107 has the general structure $[HO(EO)_a(PO)_b]_2NC_2H_4N[(PO)_c(EO)_dH]_2$ and a molecular weight of about 15,000. The subscripts a, b, c and d are approximately 59, 19, 19 and 59.

Various other ionic as well as amphoteric and anionic surfactants suitable for in the invention can be readily ascertained, in view of the foregoing description, from McCutcheon's Detergents and Emulsifiers, North American Edition, McCutcheon Division, MC Publishing Co., Glen Rock, N.J. 07452 and the CTFA International Cosmetic Ingredient Handbook, Published by The Cosmetic, Toiletry, and Fragrance Association, Washington, D.C.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

The foregoing surfactants will generally be present in a total amount from 0.01% to 5% (w/v), from 0.1% to 5% (w/v), or from 0.1% to 1.5% (w/v). Often the amount of surfactant is from 0.005% or 0.01%, to 0.1% or 0.5% or 0.8% (w/v).

The lens care compositions can also one or more neutral or basic amino acids. The neutral amino acid include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1% to 5% (w/v).

The lens care compositions can also include glycolic acid, asparatic acid or any mixture of the two at a total concentration of from 0.001% to 4% (w/v) or from 0.01% to 2.0% (w/v).

Further, the combined use of one or more amino acids and glycolic acid and/or asparatic acid can lead to a reduction in the change of the size of the contact lens due to swelling and shrinkage following placement of the lens on the eye. The stated combination provides a higher degree of compatibility with the contact lens compared to the absence of one of the two components in the composition. It is believed that one or more of the amino acids can cause the lens to swell, and that the glycolic acid and/or asparatic acid can cause the contact lens to shrink. However, if used in combination with there is believed to exist a mutual counteraction of the two observed affects, that is, the swelling and shrinkage on the lens.

The lens care compositions can also include glycolic acid, asparatic acid or any mixture of the two, in combination with 2-amino-2-methyl-1,3-propanediol or a salt thereof. One observed advantage is that compositions that contain a mixture of two of the three, or all three, compounds minimizes the change of the lens size following placement of the contact lens in the eye. It is also believed that the stated combination of compounds minimizes the amount of uptake of the cationic antimicrobial component, particularly, α-[4-tris(2-hydroxyethyl)ammonium chloride-2-butenyl]poly[1-dimethylammonium chloride-2-butenyl]-ω-tris(2-hydroxyethyl)ammonium chloride, benzalkonium halides, alexidine and salts thereof, salts of chlorhexidine, hexamethylene biguanides and salts thereof and their polymers such as poly(hexamethylene biguanide) or.

The 2-amino-2-methyl-1,3-propanediol (AMPD) or the salt thereof is added to the compositions in an amount to satisfy a predetermined molar ratio of glycolic acid, asparatic acid or any mixture of the two and AMPD. The molar ratio of the two components glycolic acid and/or asparatic acid to AMPD is 1:20 to 1.3:1. The glycolic acid, asparatic acid or any mixture of the two is present in the compositions at a concentration of 0.01% to 5% (w/v) or at a concentration of 0.05% to 1% (w/v).

If the components glycolic acid and/or asparatic acid, and AMPD, are present in the compositions in the absence of the other to the liquid preparation, one observes a tendency to cause shrinkage or swelling of the lens. However, if these two components are combined together and used in the predetermined molar ratio, little, if any, change in the size of the lens is observed.

The amount of AMPD present in the compositions can be determined according to the amount of glycolic acid and/or asparatic acid in the composition. As stated, AMPD is present in an amount to provide a molar ratio of glycolic acid and/or asparatic acid to AMPD to be from 1:20 to 1.3:1, from 1:15 to 1.2:1 or from 1:14 to 1:1. If the amount of AMPD exceeds 20 mols per 1 mol of glycolic acid and/or asparatic, adsorption of the cationic antimicrobial component on the contact lens will occur. If the amount of AMPD is less than 1 mol per 1.3 mols of glycolic acid and/or asparatic acid, a reduction in antimicrobial efficacy of the composition is observed. The viscosity inducing components used in the lens care compositions are compatible with the other components and are preferably nonionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the contact lens. The viscosity inducing component can also function to cushion the impact on the eye surface during placement of the lens and serves also to alleviate eye irritation.

Suitable viscosity inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, hydroxypropylmethyl cellulose, carboxymethyl cellulose, methyl cellulose, hydroxyethyl cellulose and the like. A very useful viscosity inducing component is hydroxypropylmethyl cellulose (HPMC).

The viscosity inducing component is used in an amount effective to increase the viscosity of the solution, preferably to a viscosity in the range of about 1.5 to about 30, or even as high as about 750, cps at 25° C., as determined by USP test method No. 911 (USP 23, 1995).

A chelating or sequestering can be included in an amount effective to enhance the effectiveness of the cationic antimicrobial component and/or to complex with metal ions to provide more effective cleaning of the contact lens. A wide range of organic acids, amines or compounds which include an acid group and an amine function are capable of acting as chelating components in the present compositions. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts, tartaric acid and its salts, and the like and mixtures thereof, are useful as chelating components.

In one embodiment, the lens care compositions include a phosphonic acid, or its physiologically compatible salt, as a chelating or sequestering agent. The phosphonic acid is represented by the following formula:

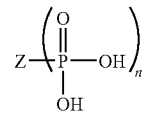

wherein Z is a connecting radical equal, n is an integer from 1 to 4, or 1, 2 or 3, and preferably containing 1 to 12 carbon atoms, more preferably 3 to 10 carbon atoms. The Z radical comprises substituted or unsubstituted saturated hydrocarbon radicals or amine-containing radicals, which amine-containing radicals are saturated hydrocarbon radicals in which the carbon atoms are interrupted with at least one nitrogen atom such as 1, 2 or 3 nitrogen atoms that forms a secondary or tertiary amine.

Accordingly, suitable Z radicals include substituted or unsubstituted alkylidene, substituted or unsubstituted alkylene, amino tri(alkylene) having at least n+1 carbon atoms, amino di(alkylene) having at least n+1 carbon atoms, alkylenediaminetetra(alkylene) or a dialkylenetriamine penta (alkylene) radical. In each case, the alkylene group in parenthesis is connected to a phosphonic acid group. Preferably, all alkylene groups independently have 1 to 4 carbon atoms.

Exemplary compounds in which the Z group is an amino tri(alkylene) radical includes amino tri(ethylidene phosphonic acid), amino tri(isopropylidene phosphonic acid), amino di(methylene phosphonic acid) mono(isopropylidene phosphonic acid), and amino mono(methylene phosphonic acid) di(ethylidene phosphonic acid). Exemplary compounds in which the Z group is a substituted or unsubstituted alkylidene radical includes methylene diphosphonic acid, ethylidine diphosphonic acid, 1-hydroxy propylidene diphosphonic acid. Exemplary compounds in which the Z group is an alkylenediaminetetra(alkylene) or a dialkylenetriamine penta (alkylene) radical include hexamethylenediaminetetra(methylene phosphonic acid) and diethylenetriaminepenta (methylenephosphonic acid).

In one embodiment, the phosphonic acid, or its physiologically compatible salt, is represented by the following formula:

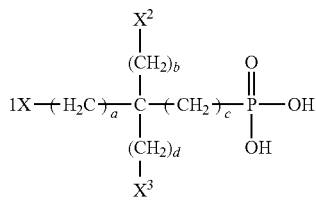

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

The lens care compositions will typically have an osmolality in the range of at least about 200 mOsmol/kg for example, about 300 or about 350 to about 400 mOsmol/kg. The lens care compositions are substantially isotonic or hypertonic (for example, slightly hypertonic) and are ophthalmically acceptable.

The lens care compositions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The contact lens can be contacted with the lens care compositions by immersing the lens in the compositions. During at least a portion of the contacting, the lens container holding the contact lens can be agitated, for example, by shaking the container to at least facilitate removal of deposit material from the lens. After such contacting step, the contact lens can be manually rubbed to remove further deposit material from the lens. The cleaning method can also include rinsing the lens substantially free of the lens care compositions prior to placing the lens on the eye.

The lens care compositions of the invention can be used with all categories of contact lenses such as hard, soft, rigid and soft gas permeable, and silicone (including both hydrogel and non-hydrogel) lenses. The compositions, however, are particularly formulated for uses with soft lenses, including soft silicone lenses. Typically, soft contact lenses are formulated from polymers having a certain proportion of repeat units derived from hydroxyethyl methacrylate and/or other hydrophilic monomers, typically crosslinked with a crosslinking agent. However, newer soft lenses, especially for extended wear, are presently prepared from high-$D_k$ silicone-containing materials.

The lens care compositions are particularly formulated as a multi-purpose solution. The multi-purpose solutions will typically include one or more antimicrobial components in sufficient concentrations to destroy harmful microorganisms on the surface of a contact lens within the recommended minimum soaking time. The recommended minimum soaking time is included in the package instructions for use of the solution.

The lens compositions can also be formulated as a preserving solution, a cleaning solution or as a storage solution of contact lenses. One of ordinary skill in the art would know how to adjust the formulation for each of these respective applications. The lens care compositions in combination with its container or bottle and packaging, including instructions for use in accordance with a specified regimen, provides an improved kit, package, or system for the care of contact lenses.

The use of the term "multi-purpose solutions" does not exclude the possibility that some patients, for example, patients particularly sensitive to chemical disinfectants or other chemical agents, may prefer to rinse or wet a contact lens with another solution, for example, a sterile saline solution prior to positioning of the lens on the eye. The term "multi-purpose solution" also does not exclude the possibility of periodic cleaners not used on a daily basis or supplemental cleaners for removing proteins, for example enzyme cleaners, which are typically used on a weekly basis.

The following non-limiting examples illustrate certain aspects of the present invention.

EXAMPLES

Ophthalmic compositions of the present invention and their foaming profiles are illustrated by the following examples.

Example 1

Prototype multi-purpose lens care compositions containing varying amounts of octoxyglycerin as a foam inhibiting agent are prepared. Such formulations differ only in the amount of octoxyglycerin used therein. The basic prototype formulation for the lens care product is shown in Table 1.

Example 2

The ability of varying small amounts of 3-[(2-ethylhexyl)oxy]-1,2-propanediol to inhibit foam formation and improve foam draining performance of the prototype lens care composition of Example I is demonstrated by means of a foam height evaluation test. In such a test, 50 mL of the solution being tested is placed in a 100 mL graduated cylinder (2.6 cm in diameter). The foam height is measured after 10 seconds of vigorous shaking of the cylinder containing the test solution. Foam height after 30 minutes of standing is also measured to evaluate foam draining propensity of the test solutions. Foam height testing results are shown in Table 2.

The Table 2 data indicate that when used in amounts over 0.05 ppm, the 3-[(2-ethylhexyl)oxy]-1,2-propanediol material can provide effective control of foaming in multi-purpose lens care products which contain over 3.0 wt % of foaming surfactants such as Pluronic® F127 and Tetronic® 1107.

TABLE 1

Formulation of a Multi-Purpose Lens Care Solution.

| Component | Concentration (wt % or ppm) |
|---|---|
| boric acid | 0.85 |
| sodium monophosphate | 0.15 |
| sodium diphosphate | 0.31 |

TABLE 1-continued

Formulation of a Multi-Purpose Lens Care Solution.

| Component | Concentration (wt % or ppm) |
|---|---|
| sodium shloride | 0.06 |
| hydroxyalkyl phosphonate (30%) | 0.1 |
| Pluronic ® F-127[1] | 3.0 |
| Tetronic ® 1107[2] | 1.5 |
| Polyquaternium-10 | 0.02 |
| alexidine | 4.5 ppm |
| octoxyglycerin | 0 to 2.0 ppm |
| purified water | Q.S. to 100 gm |

[1] Polyethylene-polypropylene glycol nonionic surfactant
[2] Polyoxyethylene-polyoxypropylene block copolymer of ethylene diamine

TABLE 2

Influence of octoxyglycerin on foaming.

| octoxyglycerin (ppm) | Foam Height (cm) Time = 0 min | Foam Height (cm) Time = 30 min |
|---|---|---|
| 0 | 7.3 ± 0.2 | 6.5 ± 0.3 |
| 0.05 | 3.8 ± 0.2 | 3.0 ± 0.3 |
| 0.10 | 2.6 ± 0.4 | 2.0 ± 0.2 |
| 0.25 | 1.3 ± 0.2 | 0.8 ± 0.2 |
| 0.50 | 0.7 ± 0.2 | 0.4 ± 0.1 |
| 0.75 | 0.3 ± 0.1 | 0.2 ± 0.1 |
| 1.00 | 0.1 ± 0.0 | 0.0 ± 0.0 |
| 2.00 | 0.1 ± 0.0 | 0.0 ± 0.0 |

The formulations described in Table 3 were prepared by dissolving all the ingredients in the order listed. Each ingredient was allowed to dissolve fully before the next ingredient was added.

The disinfection efficacy of formulations 1a, 1b and 1c was tested following the biocidal procedure outlined in ISO 14729, International Standardized Document for Ophthalmic Optics and FDA Premarket Notification (510k) Guidance Document for Contact Lens Care Products. The results of which are reported in Table 4.

As indicated by the data in Table 4, the combination of EHOPD and decanoylglycerol in a lens care multi-purpose solution provides (i) synergistic biocidal effect against Ca and Fs, and (ii) complementary effect against Sa and Sm. The compositions eliminate or reduce the amount of conventional cationic disinfectants in lens care formulations. As a result, the compositions are expected to cause less ocular irritation and be more compatible with anionic polymer excipients or contact lens materials.

TABLE 3

Lens care multi-purpose solution formulations

| | % w/w | | |
|---|---|---|---|
| Ingredient | Formulation 1a | Formulation 1b | Formulation 1c |
| boric acid | 0.64 | 0.64 | 0.64 |
| sodium borate | 0.09 | 0.09 | 0.09 |
| sodium chloride | 0.49 | 0.49 | 0.49 |
| disodium edetate | 0.10 | 0.10 | 0.10 |
| hydroxyalkyl phosphonate | 0.03 | 0.03 | 0.03 |
| poloxamine 1107 | 1.00 | 1.00 | 1.00 |
| 3-[(2-ethylhexyl)oxy]-1,2-propanediol | 0.15% | — | 0.15% |
| decanoylglycerol | — | 0.12% | 0.12% |
| water | q.s. to 100% | q.s. to 100% | q.s. to 100% |
| pH | 7.1-7.5 | 7.1-7.5 | 7.1-7.5 |
| osmolality, mOsm/Kg | 280-320 | 280-320 | 280-320 |

Example 3

PHMB (Polyamino propyl Biguanide Hydrochloride, 2 g, 0.0011 mole,) and HMBDA (1,6-bis(cyanoguanadino)hexane, 0.3 g, 0.0012 mole were mixed and ground together, then placed in a 100 mL round bottom flask. Concentrated Hydrochloric acid (100 μL) was then added to the PHMB/HMBDA. The mixture was slowly heated to 100° C. until all the liquid was driven off. The heat was then increased to 150° C. to 160° C. and held for 4 hours. The reaction mixture was cooled to room temperature providing 1.32 g of the crystalline material PHMB-CG*.

TABLE 4

Biocidal results of multi-purpose formulations containing EHOPD and decanoylglycerol.

| Formulation | Time point | Log Reduction | | | | |
|---|---|---|---|---|---|---|
| | | Sa[1] | Pa[2] | Sm[3] | Ca[4] | Fs[5] |
| 1a | 30 min | 1.4 | >4.7 | >4.7 | 0.2 | 1.0 |
| | 4 hour | 1.5 | >4.7 | >4.7 | 0.5 | 2.0 |
| 1b | 30 min | 1.6 | >4.7 | 1.8 | 0.8 | 2.7 |
| | 4 hour | 3.6 | >4.7 | 1.8 | >4.8 | >4.6 |
| 1c | 30 min | 1.9 | >4.7 | >4.7 | 2.8 | >4.6 |
| | 4 hour | >4.9 | >4.7 | >4.7 | >4.8 | >4.6 |

[1] *Staphylococcus aureus* (ATCC 6538)
[2] *Pseudomonas aeruginosa* (ATCC 9027)
[3] *Serratia marcescens* (ATCC 13880)
[4] *Candida albicans* (ATCC 10231)
[5] *Fusarium Solani* (ATCC 36031)

We claim:

1. An aqueous ophthalmic composition comprising:
    a branched, glycerol monoalkyl compound;
    a fatty acid monoester, wherein the fatty acid monoester comprises an aliphatic fatty acid portion having six to fourteen carbon atoms and an aliphatic hydroxyl portion;
    and a cationic antimicrobial component selected from the group consisting of poly[dimethylimino-2-butene-1,4-diyl]chloride, α-[4-tris(2-hydroxyethyl)ammonium chloride-2-butenyl]poly[1-dimethyl ammonium chloride-2-butenyl]-ω-tris(2-hydroxyethyl)ammonium chloride, myristamidopropyl dimethylamine, benzalkonium halides, alexidine and salts thereof, salts of chlorhexidine, hexamethylene biguanides and salts thereof and their polymers, and mixtures thereof, said composition having an osmolality in a range from 200 mOsmol/kg to 400 mOsmol/kg.

2. The composition of claim 1 wherein the branched, glycerol monoalkyl compound is selected from a branched, glycerol monoalkyl ether, a branched, glycerol monoalkyl amine or a branched, glycerol monoalkyl sulfide, or any mixture thereof.

3. The composition of claim 1 wherein the aliphatic fatty acid portion is a straight chain, saturated or unsaturated hydrocarbon with eight to ten carbons, or a branched chain, saturated or unsaturated hydrocarbon with eight to ten carbons.

4. The composition of claim 1 wherein the aliphatic hydroxyl portion is selected from propylene glycol, polyethylene glycol, polypropylene glycol, glycerol, linear polyol and cyclic polyol.

5. The composition of claim 4 wherein the aliphatic hydroxyl portion is glycerol.

6. The composition of claim 1 wherein the branched, glycerol monoalkyl compound is 3-[(2-ethylhexyl)oxy]-1,2-propanediol, 3-[(2-ethylhexyl)amino]-1,2-propanediol, 3-[(2-ethylhexyl)thiol]-1,2-propanediol or any mixture thereof.

7. The composition of claim 1 wherein the cationic antimicrobial component is selected from the group consisting of poly(hexamethylene biguanide) or PHMB-CG*, which is present from 0.01 ppm to 3 ppm, α-[4-tris(2-hydroxyethyl) ammonium chloride-2-butenyl]poly[1-dimethylammonium chloride-2-butenyl]-ω-tris(2-hydroxyethyl) ammonium chloride, which is present from 1 ppm to 100 ppm, and any mixture thereof.

8. The composition of claim 3 further comprising dexpanthenol, sorbitol or any mixture thereof.

9. The composition of claim 3 further comprising 2-amino-2-methyl-1,3-propanediol, and glycolic acid, asparatic acid or a mixture thereof, wherein a molar ratio of the total glycolic acid, asparatic acid or mixture thereof to AMPD is from 1:20 to 1.3:1.

10. The composition of claim 1 formulated in the form of an eye care or a contact lens care product selected from the group consisting of eye drops, contact lens preservative solution, contact lens cleaning solution, and contact lens multipurpose solution.

11. The composition of claim 1 formulated as a contact lens multi-purpose solution to disinfect a soft contact lens.

12. A method of inhibiting the formation of foam in an aqueous ophthalmic composition comprising a fatty acid monoester, wherein the fatty acid monoester comprises an aliphatic fatty acid portion having six to fourteen carbon atoms and an aliphatic hydroxyl portion, the method comprising adding a branched, glycerol monoalkyl compound to the composition in an amount from 0.05 ppm to 30.0 ppm to inhibit the formation of foam or to destabilize foam in the composition, the composition further comprising a cationic antimicrobial component selected from the group consisting of poly[dimethylimino-2-butene-1,4-diyl]chloride, α-[4-tris(2-hydroxyethyl)ammonium chloride-2-butenyl]poly[1-dimethylammonium chloride-2-butenyl]-ω-tris(2-hydroxyethyl)ammonium chloride, myristamidopropyl dimethylamine, benzalkonium halides, alexidine and salts thereof, salts of chlorhexidine, hexamethylene biguanides and salts thereof and their polymers, and mixtures thereof, and having an osmolality in a range from 200 mOsmol/kg to 400 mOsmol/kg.

13. The method of claim 12 wherein the branched, glycerol monoalkyl compound is selected from a branched, glycerol monoalkyl ether, a branched, glycerol monoalkyl amine or a branched, glycerol monoalkyl sulfide, or any mixture thereof.

14. The method of claim 12 wherein the cationic antimicrobial component is selected from the group consisting of poly(hexamethylene biguanide), which is present from 0.01 ppm to 3 ppm, α-[4-tris(2-hydroxyethyl)ammonium chloride-2-butenyl]poly[1-dimethylammonium chloride-2-butenyl]-ω-tris(2-hydroxyethyl)ammonium chloride, which is present from 1 ppm to 100 ppm, and any mixture thereof.

15. A method of enhancing the biocidal efficacy of an aqueous ophthalmic composition containing a fatty acid monoester, the method comprising adding a branched, glycerol monoalkyl compound to the composition, and adding one or more cationic antimicrobial components selected from the group consisting of poly[dimethylimino-2-butene-1,4-diyl]chloride, α-[4-tris(2-hydroxyethyl)ammonium chloride-2-butenyl]poly[1-dimethylammonium chloride-2-butenyl]-ω-tris(2-hydroxyethyl)ammonium chloride, myristamidopropyl dimethylamine, benzalkonium halides, alexidine and salts thereof, salts of chlorhexidine and hexamethylene biguanides and salts thereof and their polymers, to the composition, wherein the cationic antimicrobial component is added in an effective amount to provide a contact lens multipurpose solution to disinfect soft silicon lenses, wherein the wherein the fatty acid monoester comprises an aliphatic fatty acid portion having six to fourteen carbon atoms and an aliphatic hydroxyl portion, and the composition has an osmolality in a range from 200 mOsmol/kg to 400 mOsmol/kg.

16. The method of claim 15 wherein the one or more cationic antimicrobial components are selected from the group consisting of poly(hexamethylene biguanide) or PHMB-CG*, which is present from 0.01 ppm to 3 ppm, and α-[4-tris(2-hydroxyethyl)ammonium chloride-2-butenyl] poly[1-dimethylammonium chloride-2-butenyl]-ω-tris(2-hydroxyethyl)ammonium chloride, which is present from 1 ppm to 100 ppm.

17. The method of claim 15 wherein the branched, glycerol monoalkyl compound is selected from a branched, glycerol monoalkyl ether, a branched, glycerol monoalkyl amine, a branched, glycerol monoalkyl sulfide, or any mixture thereof, and is present in a total amount from 0.05 ppm to 1,000 ppm.

* * * * *